United States Patent
Omote

(10) Patent No.: US 7,116,755 B2
(45) Date of Patent: *Oct. 3, 2006

(54) NON-UNIFORM DENSITY SAMPLE ANALYZING METHOD, DEVICE AND SYSTEM

(75) Inventor: Kazuhiko Omote, Akishima (JP)

(73) Assignee: Rigaku Corporation, Tokyo (JP)

( * ) Notice: Subject to any disclaimer, the term of this patent is extended or adjusted under 35 U.S.C. 154(b) by 68 days.

This patent is subject to a terminal disclaimer.

(21) Appl. No.: 10/482,022

(22) PCT Filed: Jun. 17, 2002

(86) PCT No.: PCT/JP02/06013

§ 371 (c)(1),
(2), (4) Date: May 20, 2004

(87) PCT Pub. No.: WO03/002997

PCT Pub. Date: Jan. 9, 2003

(65) Prior Publication Data

US 2004/0195498 A1    Oct. 7, 2004

(30) Foreign Application Priority Data

Jun. 27, 2001    (JP)    ............... 2001-195112

(51) Int. Cl.
*G01N 23/201*    (2006.01)
(52) U.S. Cl. .......................................... 378/86; 378/70
(58) Field of Classification Search .................. 378/70, 378/71, 76, 86, 89, 90, 73, 75, 88
See application file for complete search history.

(56) References Cited

U.S. PATENT DOCUMENTS 5,200,910 A * 4/1993 Subbiah ..................... 703/2

(Continued)

FOREIGN PATENT DOCUMENTS

JP    8-145916    6/1996

(Continued)

OTHER PUBLICATIONS

"Advanced Thin film X-ray system-Grazing incidence in-plane diffractometer". The Rigaku Journal 16 (1), 53-58 (1999).*

(Continued)

*Primary Examiner*—Allen C. Ho
(74) *Attorney, Agent, or Firm*—Wenderoth, Lind & Ponack, L.L.P.

(57) ABSTRACT

A non-uniform density sample analyzing method for analyzing a distribution state of particle-like matter in a non-uniform density sample, where an actually measured X-ray scattering curve is an in-plane X-ray scattering curve obtained by in-plane diffraction measurement, and fitting between the in-plane X-ray scattering curve and the simulated X-ray scattering curve is performed. The value of the fitting parameter when the simulated X-ray scattering curve agrees with the in-plane X-ray scattering curve serves to indicate the in-plane direction distribution sate of the particle-like matter in the non-uniform density sample. This method can analyze the in-plane direction distribution state of the particle-like matter in the anisotropic non-uniform density sample easily and accurately. Its device and system are also disclosed.

6 Claims, 12 Drawing Sheets

U.S. PATENT DOCUMENTS

| | | | |
|---|---|---|---|
| 5,442,676 A * | 8/1995 | Fewster | 378/72 |
| 5,530,732 A * | 6/1996 | Takemi | 378/73 |
| 6,192,103 B1 * | 2/2001 | Wormington et al. | 378/73 |
| 6,823,043 B1 * | 11/2004 | Fewster et al. | 378/86 |
| 6,895,075 B1 * | 5/2005 | Yokhin et al. | 378/90 |
| 6,920,200 B1 * | 7/2005 | Ito et al. | 378/89 |
| 6,937,694 B1 | 8/2005 | Yokoyama et al. | 378/78 |
| 7,035,373 B1 * | 4/2006 | Omote | 378/79 |
| 7,039,161 B1 * | 5/2006 | Ito et al. | 378/86 |
| 2003/0157559 A1 | 8/2003 | Omote et al. | 435/7.1 |

FOREIGN PATENT DOCUMENTS

| | | |
|---|---|---|
| JP | 2001-56304 | 2/2001 |
| JP | 2001-349849 | 12/2001 |

OTHER PUBLICATIONS

Kazuhiko Omote and Shin-Ya Matsuno. Advances in X-Ray Chemical Analysis, Japan 30, 205-218 (1999).*

Hirokatsu Miyata and Kazuyuki Kuroda, Chemistry of Materials, Formation of a Continuous Mesoporous Silica Film with Fully Aligned Mesochannels and a Glass Substrate, vol. 12, No. 1, pp. 49-54, 2000.

* cited by examiner

(a)

(b)

(a)

(b)

(a)

(b)

(c)

NON-UNIFORM DENSITY SAMPLE ANALYZING METHOD, DEVICE AND SYSTEM

BACKGROUND OF THE INVENTION

1. Technical Field of the Invention

The present invention relates to a method, device and system for analyzing a non-uniform density sample, and more particularly, to a novel non-uniform density sample analyzing method, non-uniform density sample analyzing device and non-uniform density sample analyzing system which are capable of simply and accurately analyzing an in-plane direction distribution state of particle-like matter in the non-uniform density sample.

2. Description of the Related Art

A method for analyzing a particle diameter distribution in a non-uniform density sample such as a porous film by using an X-ray has been newly proposed by the inventors of the present invention (see Japanese Patent Application No. 2001-088656). In this method, a diffuse scattering intensity of the X-ray is measured and the particle diameter distribution is analyzed based on the measured intensity, thereby realizing an excellent analyzing ability.

However, there is yet room for improvement in such an excellent analyzing method so as to achieve another new advantage.

That is, with the non-uniform density sample analyzing method disclosed in the Japanese Patent Application No. 2001-088656, it is difficult to completely analyze the density non-uniformity of an anisotropic non-uniform density sample.

To be specific, a non-anisotropic non-uniform density sample is a sample in which particle-like matter such as a fine particle and pore has a random distribution as shown in, for example, FIG. 1(a). Conversely, as shown in, for example, FIGS. 2(a) and 2(b), an anisotropic non-uniform density sample is a sample in which the distribution of particle-like matter has some regularity or directivity in an in-plane direction. In the example of FIG. 2(b), the particle-like matter is distributed in the in-plane direction with regularity in which clusters each having two pentagons connected to each other are formed.

As for the non-anisotropic non-uniform density sample, if an X-ray scattering curve is measured by scanning an X-ray outgoing angle $\theta_{out}$ with an X-ray incident angle $\theta_{in}$ being constant in a condition of, for example, $\theta_{in}=\theta_{out}+$offset $\Delta\Omega$, the density non-uniformity of the sample in a direction corresponding to a direction of a scattering vector q shown in FIGS. 1(a) and 1(b), i.e., a direction near a normal plane is measured as described in the Japanese Patent Application No. 2001-088656. This is a so-called out-of-plane diffraction measurement.

If this out-of-plane diffraction measurement is directly applied to the anisotropic non-uniform density sample, the non-uniformity of the sample is measured along the scattering vector q in the direction near the normal plane shown in FIGS. 2(a) and 2(b) similar to FIG. 1. This means that the anisotropic non-uniform density sample cannot be analyzed in an in-plane direction of the sample. By contrast, the in-plane direction of the sample is random with the non-anisotropic non-uniform density sample. Therefore, even if a scan direction is changed, the particle-like matter can be observed without any changes and thus no disadvantage occurs. With the anisotropic non-uniform density sample, however, because of the regularity of the particles in the in-plane direction as described above, the particle-like matter is observed differently according to the scan direction. As a result, the particle diameter distribution in the in-plane direction cannot be analyzed with the out-of-plane diffraction measurement.

The present invention has been achieved in light of these situations. Accordingly, an object of the present invention to provide a novel non-uniform density sample analyzing method as well as a non-uniform density sample analyzing device and a non-uniform density sample analyzing system which are capable of simply and highly accurately analyzing the distribution state of the particle-like matter in an anisotropic non-uniform density sample in the in-plane direction.

SUMMARY OF THE INVENTION

In order to achieve the foregoing, a first aspect of the present invention provides a non-uniform density sample analyzing method comprising the steps of calculating a simulated X-ray scattering curve under the same condition as a measurement condition of an actually measured X-ray scattering curve by using a scattering function which represents an X-ray scattering curve according to a fitting parameter which indicates distribution state of particle-like matter, and carrying out fitting between the simulated X-ray scattering curve and the actually measured X-ray scattering curve while changing the fitting parameter. The value of the fitting parameter when the simulated X-ray scattering curve agrees with the actually measured X-ray scattering curve serves to indicate the distribution state of the particle-like matter in a non-uniform density sample, thereby analyzing the distribution state of the particle-like matter in the non-uniform density sample. The actually measured X-ray scattering curve is an in-plane X-ray scattering curve obtained by in-plane diffraction measurement, and the fitting is carried out between the in-plane X-ray scattering curve and the simulated X-ray scattering curve. Moreover, the value of the fitting parameter when the simulated X-ray scattering curve agrees with the in-plane X-ray scattering curve serves to indicate the in-plane direction distribution state of the particle-like matter in the non-uniform density sample.

A second aspect of the present invention also provides the analyzing method in which the fitting parameter of the scattering function indicates the in-plane direction distribution state of the particle-like matter.

Further, a third aspect of the present invention provides a non-uniform density sample analyzing device comprising function storage means for storing a scattering function which represents an X-ray scattering curve according to a fitting parameter which indicates a distribution state of particle-like matter, simulation means for calculating a simulated X-ray scattering curve in the same condition as a measurement condition of an actually measured X-ray scattering curve by using the scattering function stored in the function storage means, and fitting means for carrying out fitting between the simulated X-ray scattering curve and the actually measured X-ray scattering curve while changing the fitting parameter. The value of the fitting parameter when the simulated X-ray scattering curve agrees with the actually measured X-ray scattering curve serves to indicate the distribution state of the particle-like matter in a non-uniform density sample, where the actually measured X-ray scattering curve is an in-plane X-ray scattering curve obtained by in-plane diffraction measurement. The fitting is carried out between the in-plane X-ray scattering curve and the simulated X-ray scattering curve, and the value of the fitting parameter when the simulated X-ray scattering curve agrees with the in-plane X-ray scattering curve serves to indicate the in-plane direction distribution state of the particle-like matter in the non-uniform density sample. A fourth aspect of the present invention also provides the analyzing device in which the fitting parameter of the scattering function indicates the in-plane direction distribution state of the particle-like matter.

Moreover, a fifth aspect of the present invention provides a non-uniform density sample analyzing system for analyzing the distribution state of particle-like matter in a non-uniform density sample. The non-uniform density sample analyzing system comprises an in-plane diffraction measuring device which performs in-plane diffraction measurement of an actually measured X-ray scattering curve for the non-uniform density sample, and the non-uniform density sample analyzing device according to the above-described third or fourth aspect.

Figure 1:
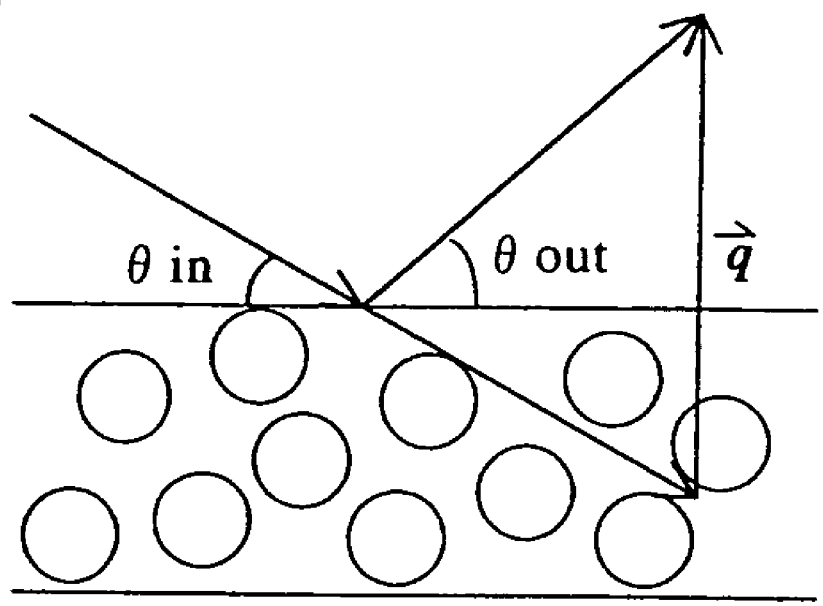
FIGS. 1(a) and 1(b) are each illustrations for explaining an out-of-plane diffraction measurement conducted to a non-anisotropic non-uniform density sample.
Figure 1:
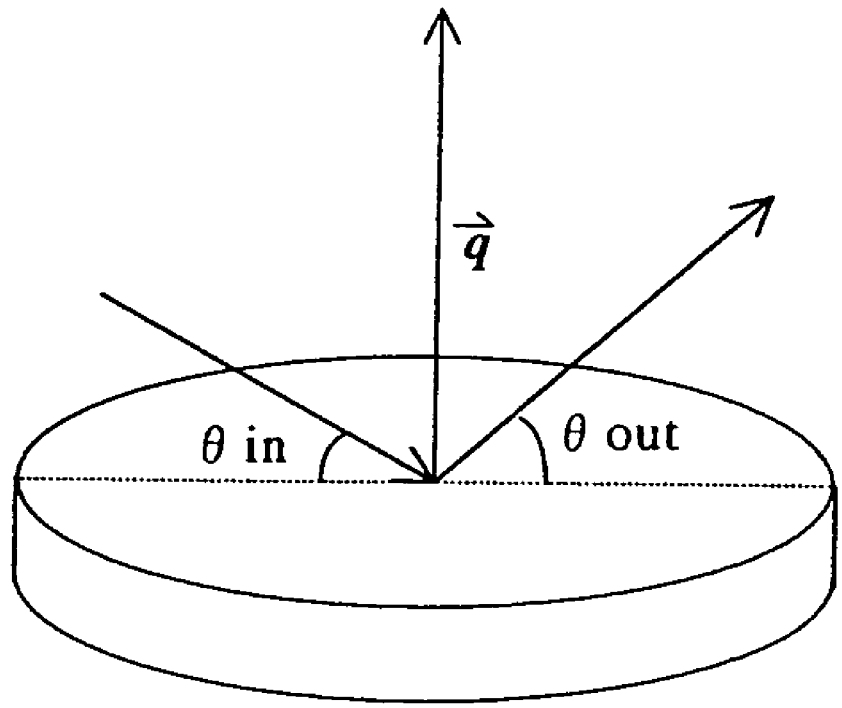
Figure 2:
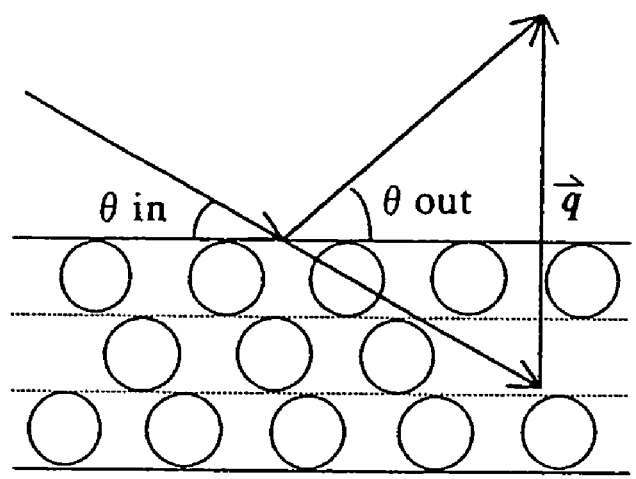
FIGS. 2(a) and 2(b) are each illustrations for explaining an out-of-plane diffraction measurement conducted to an anisotropic non-uniform density sample.
Figure 2:
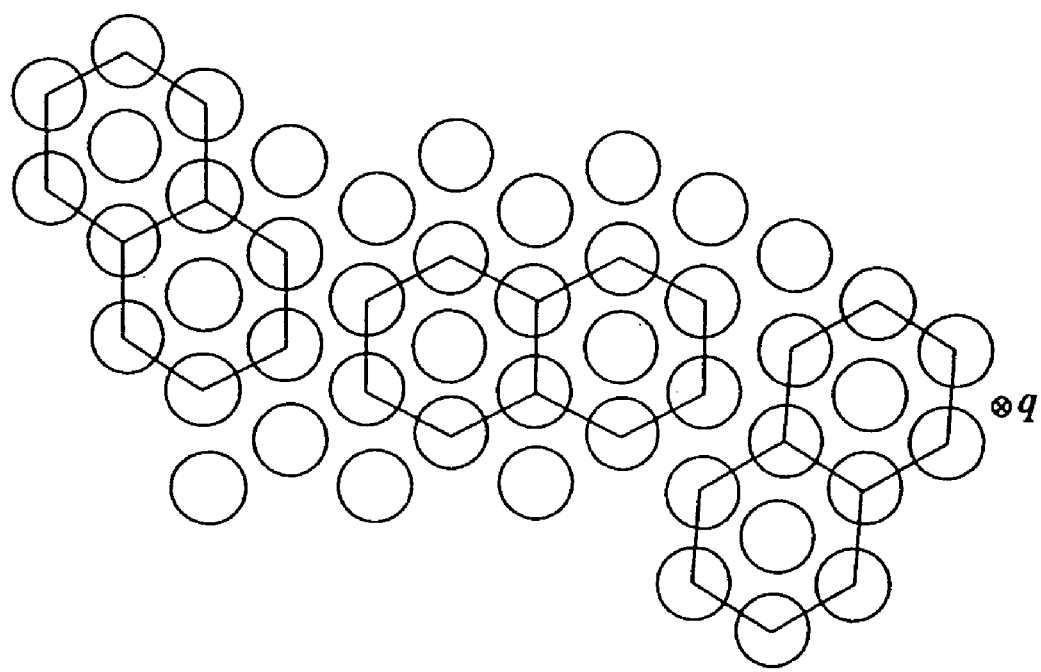

Reference symbols in the drawings denote the following system, device, or
1 Non-uniform density sample analyzing system
2 X-ray measuring device
3 Non-uniform density sample analyzing device
   31 Critical angle storage means
   32 Function storage means
   34 Fitting means
   35,36 Output means
   301 Function storage means
   302 Simulation means
   303 Fitting means
   304, 305 Output means
4 In-plane diffraction measuring device

DESCRIPTION OF THE INVENTION

The present invention applies an in-plane diffraction measurement to the non-uniform density sample analyzing method described in Japanese Patent Application No. 2001-088656 so as to realize an analysis of an anisotropic non-uniform density sample in an in-plane direction.

Figure 3:
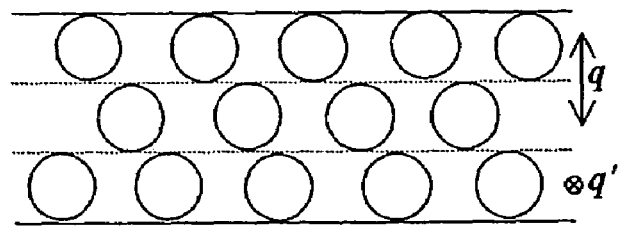
FIGS. 3(a), 3(b), and 3(c) are each illustrations for explaining an in-plane diffraction measurement conducted to the anisotropic non-uniform density sample.
Figure 3:
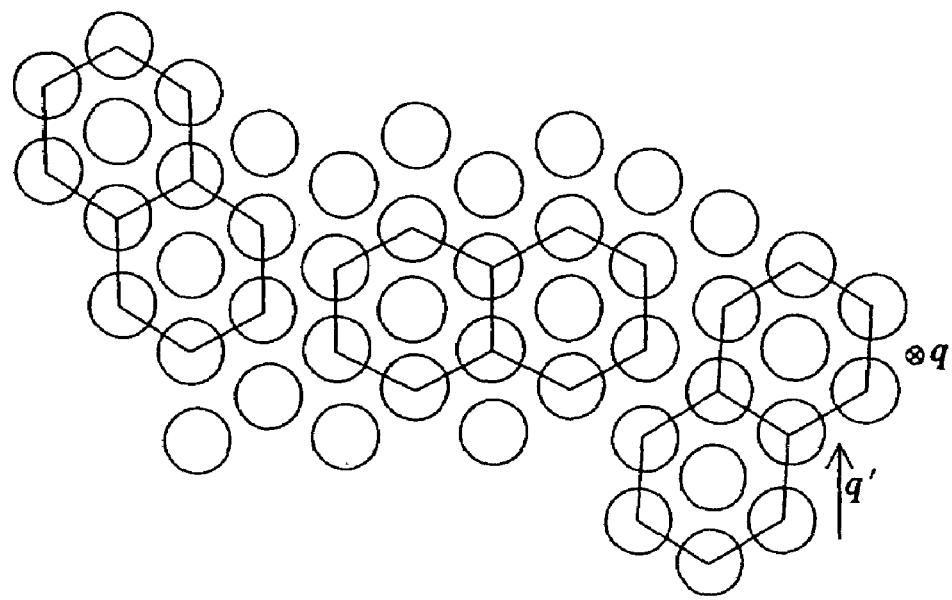
Figure 3:
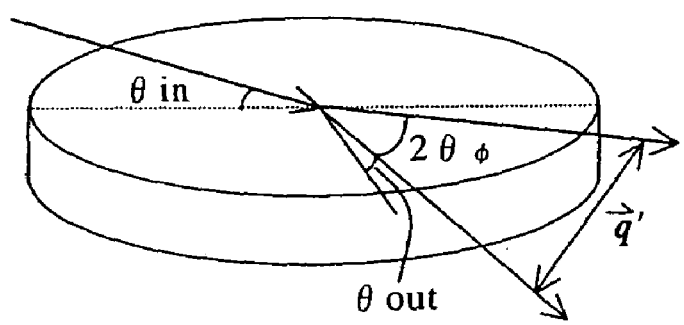

As shown in FIG. 3(c), the in-plane diffraction measurement utilizes in-plane diffraction wherein if an X-ray is incident on a surface of a sample at a very small incident angle $\theta_{in}$, then an X-ray component in parallel to the sample surface appears in the sample, the X-ray component is diffracted by a crystal surface perpendicular to the sample surface and diffracted in a plane at a diffraction angle $2\theta_o$, and a diffraction line of the diffracted X-ray component is emitted at a very small angle $\theta_{out}$, relative to the sample surface.

According to this in-plane diffraction measurement, as shown in FIGS. 3(a) and 3(b), a scattering vector q' in the in-plane direction of the non-uniform density sample can be measured. Therefore, by employing the scattering vector q' (hereinafter, "in-plane X-ray scattering curve") as an actually measured X-ray scattering curve in the non-uniform density analyzing method described in Japanese Patent Application No. 2001-088656, the distribution state of the particle-like matter in the in-plane direction can be analyzed accurately.

Figure 4:
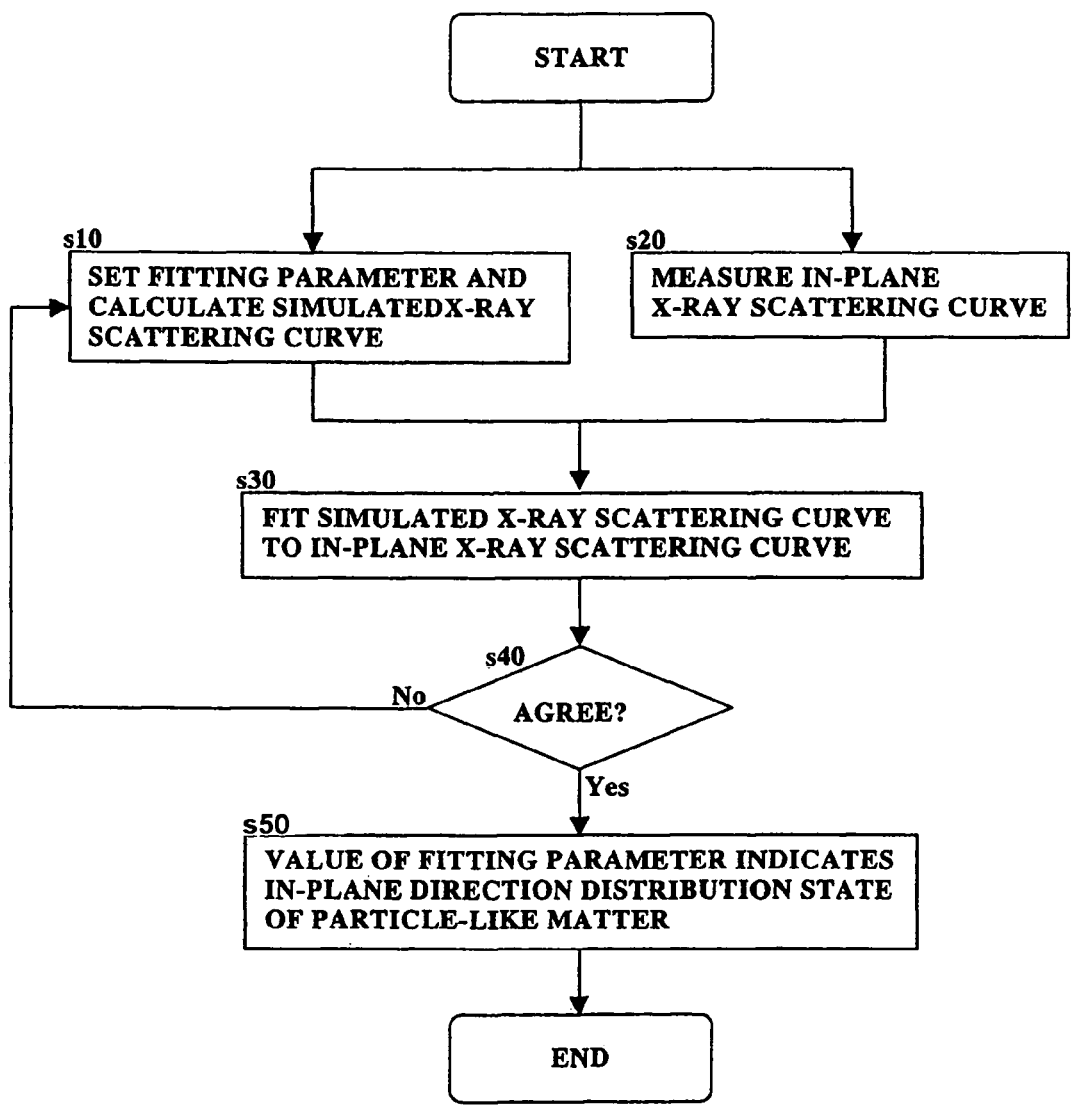
FIG. 4 is a flow chart for explaining a non-uniform density sample analyzing method according to the present invention.
Figure 11:
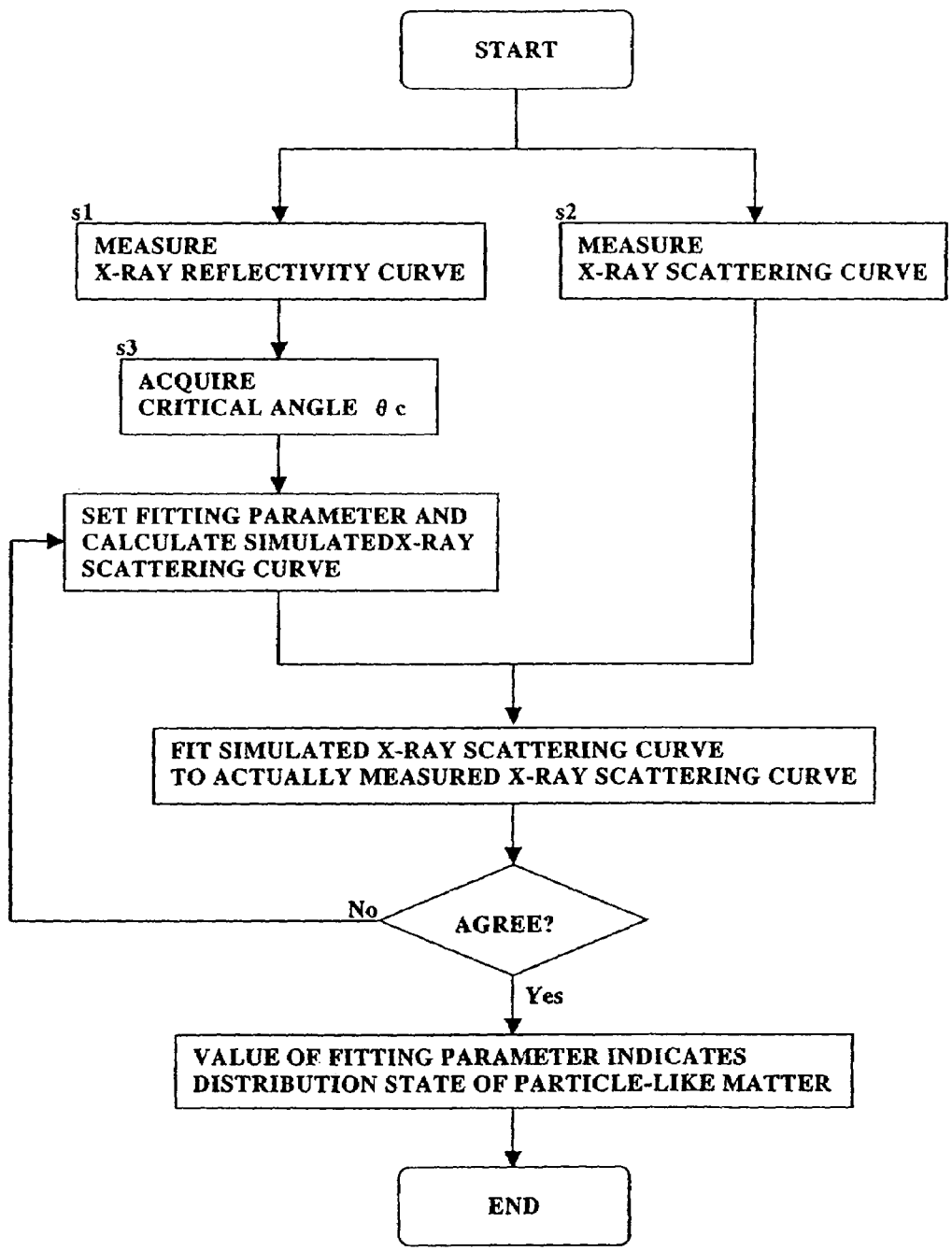
FIG. 11 is a flow chart for explaining a non-uniform density sample analyzing method described in Japanese Patent Application No. 2001-088656.

FIG. 4 is a flow chart for explaining the non-uniform density sample analyzing method of the present invention using the in-plane diffraction measurement. As shown in FIG. 4, with the analyzing method of the present invention, the measurement of the X-ray scattering curve in Step s2 of the non-uniform density analyzing method described in Japanese Patent Application No. 2001-088652 shown in FIG. 11 is made by the in-plane diffraction measurement (Step s20). Then, the fitting between the measured in-plane X-ray scattering curve and a simulated X-ray scattering curve calculated separately (Step s10) is performed (Step s30), and the value of the fitting parameter obtained when the simulated x-ray scattering curve and the in-plane X-ray scattering curve agree with each other serves to indicate the distribution state of the particle-like matter in the non-uniform density sample in the in-plane direction (Steps s40 and s50).

The simulated X-ray scattering curve is calculated (Step s10) by using a scattering function that represents an X-ray scattering curve according to the fitting parameter that indicates the distribution state of the particle-like matter and by arbitrarily selecting the value of the fitting parameter. In this case, according to the present invention, since the distribution state of the particle-like matter in the in-plane direction is to be analyzed, the fitting parameter that represents the distribution state of the particle-like matter in the in-plane direction is used. The following Eq. 1 illustrates one example of the scattering function to which the fitting parameters that represent the distribution state of the particle-like matter in the in-plane direction are introduced.

Eq. 1:

$$I(q) = S(q) \cdot I_0(q)$$

$$q = \frac{4\pi}{\lambda} \sin \theta_\phi$$

-continued $$S(q) = \frac{1}{1 - C(q \times D, \eta)}$$

$$C(x, \eta) = -\frac{24\eta}{(1-\eta)^4 x^3} \begin{bmatrix} (1+2\eta)^2(\sin x - x\cos x) - \\ 6\eta\left(1+\frac{\eta}{2}\right)^2\left(2\sin x - x\cos x - 2\frac{1-\cos x}{x}\right) + \\ \frac{\eta}{2}\left(1+\frac{\eta}{2}\right)^2\left\{\left(4-\frac{24}{x^2}\right)\sin x - \\ \left(x-\frac{12}{x}\right)\cos x + 24\frac{1-\cos x}{x^3}\right\} \end{bmatrix}$$

$$I_o(q, R_o, M) = \frac{8\pi^2 r^2 |\bar{f}(q)|^2 \left(1 + \frac{4q^2 R_o^2}{M^2}\right)^{-\frac{1+M}{2}}}{(-3+M)(-2+M)(-1+M) \cdot q^6} \times$$

$$\begin{bmatrix} M^3\left(1+\frac{4q^2R_o^2}{M^2}\right)^{-\frac{1+M}{2}} - \\ M^3\left(1-\frac{4q^2R_o^2}{M^2}\right)\cos\left((-1+M)\tan^{-1}\left(\frac{2qR_o}{M}\right)\right) + \\ (-3+M)(-2+M)M \cdot q^2 R_o^2 \cos\left((-1+M)\tan^{-1}\left(\frac{2qR_o}{M}\right)\right) + \\ \left(1+\frac{4q^2R_o^2}{M^2}\right)^{-\frac{1+M}{2}} + \\ (-3+M)M^3 \frac{4q^2R_o^2}{M^2}\cos\left((-1+M)\tan^{-1}\left(\frac{2qR_o}{M}\right)\right) - \\ 2(-1+M)M^2 qR_o \sin\left((-1+M)\tan^{-1}\left(\frac{2qR_o}{M}\right)\right) \end{bmatrix}$$

where:

$q=|q|$: Magnitude of scattering vector, $q$: Scattering vector, $\lambda$: X-ray wavelength, $R_o$: Mean diameter parameter of particle-like matter, M: Distribution shape parameter, D: Shortest distance parameter between particle-like matters, and $\eta$: Correlation order parameter of particle-like matter.

The fitting parameters of the scattering function given in this Eq. 1 are the mean diameter parameter $R_o$ of the particle-like matter, the distribution shape parameter M, the shortest distance parameter D between the particle-like matters, and the correlation order parameter $\eta$ of the particle-like matter.

Naturally, it is necessary to calculate the simulated X-ray scattering curve in the same conditions as those for the scattering curve. Therefore, the conditions are set equal to in-plane diffraction measurement conditions.

In the in-plane diffraction, there is no need to measure a reflectivity curve. Due to this, Steps s1 and s3 shown in FIG. 11 are removed from the flow chart of FIG. 4.

In Steps s30 and s40, it is determined whether or not the simulated X-ray scattering curve agrees with the in-plane X-ray scattering curve. If they do not agree, then the values of the fitting parameters are changed, the simulated X-ray scattering curve is recalculated, and it is determined whether or not the recalculated simulated X-ray scattering curve agrees with the in-plane scattering curve.

These steps are repeated while adjusting and changing the values of the fitting parameters until the both curves agree with each other. The values of the fitting parameters obtained when they agree are values that represent the in-plane direction distribution state of the particle-like matter in the non-uniform density sample of the analysis target (Step s50). In case of the Eq. 1, the mean diameter $R_o$, the distribution shape M, the shortest distance D, and the correlation order $\eta$ of the particle-like matter are analyzed in the in-plane direction.

With this non-uniform density sample analyzing method, the X-ray incident angle $\theta_{in}$ is variously changed during the in-plane diffraction measurement and the penetrating depth of the X-ray in the sample is changed, and as a result, the in-plane direction distribution of the particle-like matter at any depth position in the sample can be analyzed.

Figure 7:
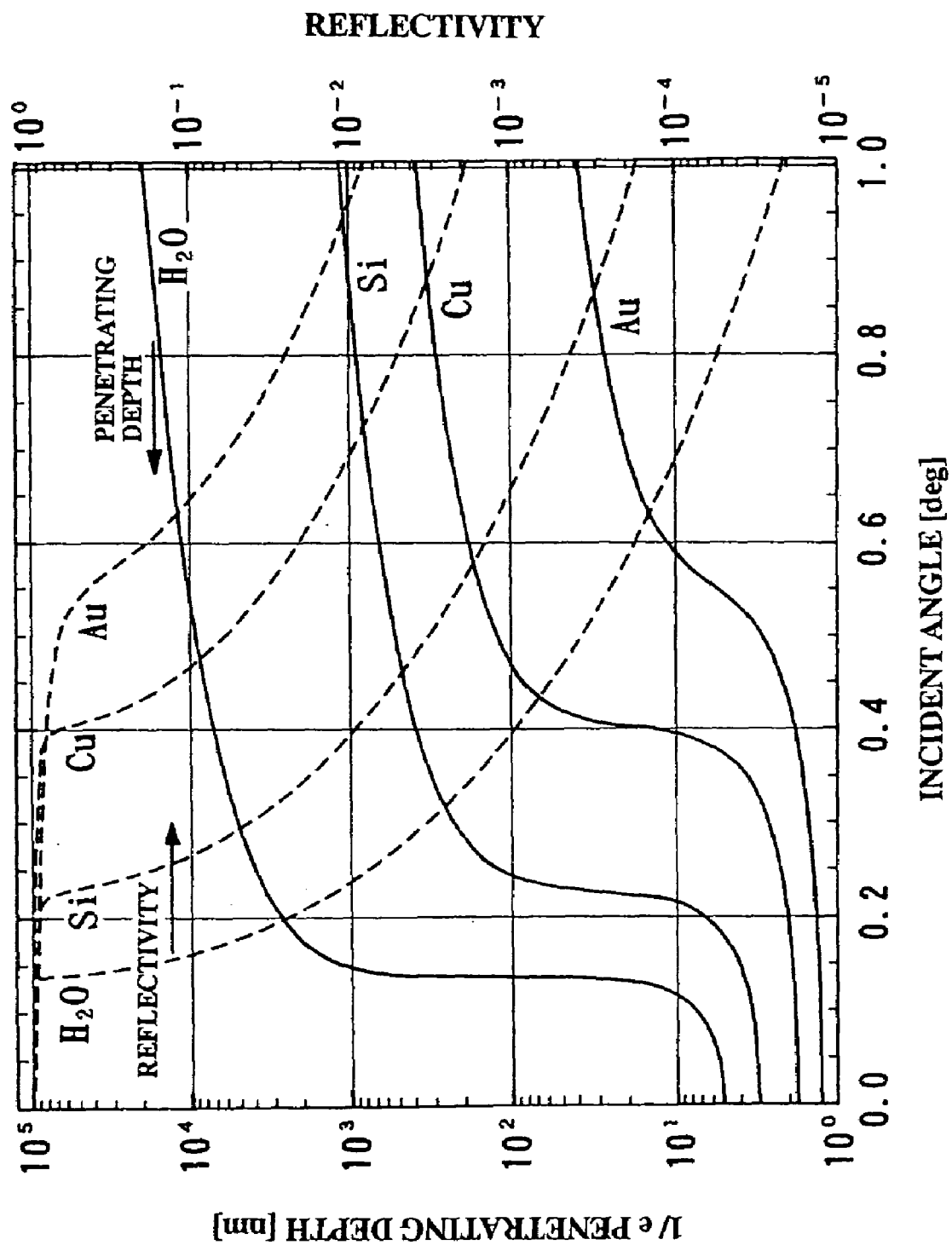
FIG. 7 illustrates the relationship among an X-ray incident angle, a penetrating depth, and a reflectivity.

FIG. 7 illustrates one example of a change in the penetrating depth [nm] relative to the X-ray incident angle $\theta_{in}$. As can be seen from FIG. 7, if the X-ray is incident on an Si surface at, for example, 0.1°, the penetrating depth of the X-ray is only 3 nanometers. If the in-plane diffraction measurement is made in this state, the in-plane direction distribution on a very thin surface of the penetrating depth of 3 nanometers can be analyzed. If the incident angle is set at about 0.3°, then the penetrating depth exceeds 200 nanometers and a structural analysis within the range of this depth can be performed. If the sample is a thin film, the structure of the thin film often changes on a surface and an inside thereof. Therefore, the analysis of the sample in the depth direction by variously changing the X-ray incident angle is quite effective. For example, it is possible to simply and accurately determine whether or not the film is formed uniformly in the depth direction.

Figure 5:
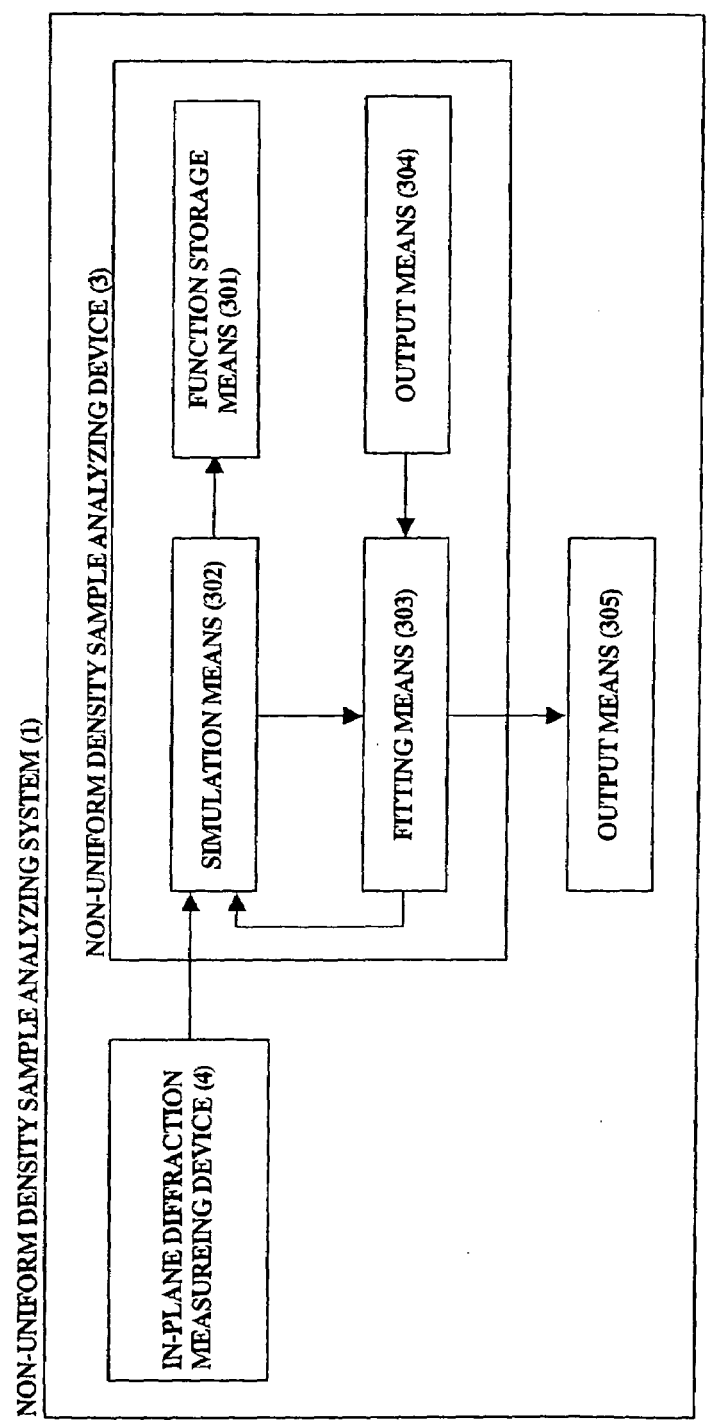
FIG. 5 is a block diagram for explaining a non-uniform density sample analyzing device and a non-uniform density sample analyzing system according to the present invention.
Figure 6:
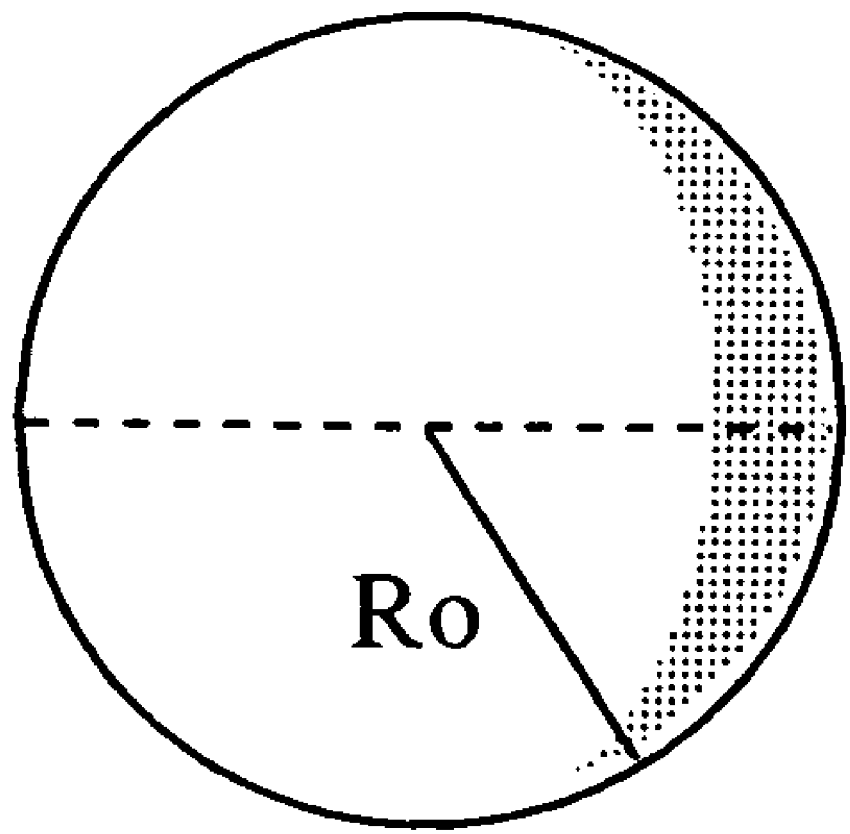
FIG. 6 illustrates a particle diameter model as a shape model of particle-like matter.
Figure 12:
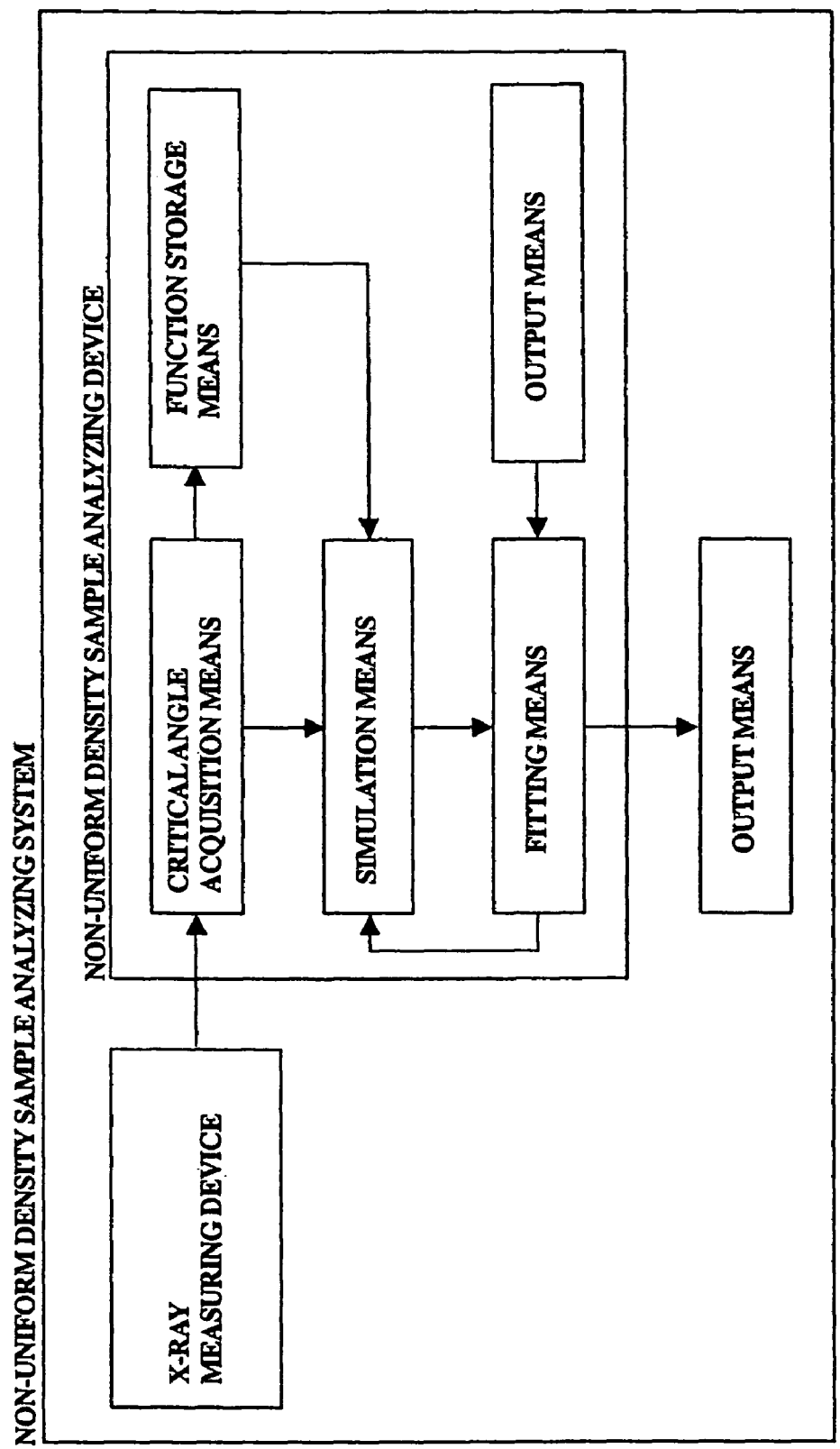
FIG. 12 is a block diagram for explaining a non-uniform density sample analyzing device and a non-uniform density sample analyzing system described in Japanese Patent Application No. 2001-088656.

FIG. 5 is a block diagram for explaining a non-uniform density sample analyzing device 3 for executing the non-uniform density sample analyzing method described above and a non-uniform density analyzing system 1 that includes the non-uniform density analyzing device 3. As illustrated in FIG. 5, the analyzing system 1 according to the present invention includes an in-plane diffraction measurement device (4) that measures in-plane diffraction in place of an X-ray measurement device (2) in the non-uniform density analyzing system described in Japanese Patent Application No. 2001-088656 shown in FIG. 12.

As the in-plane diffraction measurement device (4), a conventional, well-known device can be employed. For example, a device proposed by the present inventor (see Japanese Patent Application Laid-Open No. 11-287773) is known as one such device. The device disclosed in Japanese Patent Application Laid-Open No. 11-287773 is constituted so that a parabolic multilayer monochromator formed by alternately providing heavy element layers and light element layers a plurality of times and having a surface, on which an X-ray is incident, formed as a paraboloid so as to facilitate creating a parallel X-ray beam having a large intensity and to realize highly reliable in-plane diffraction measurement even at an experimental level and so that a goniometer capable of scanning the X-ray not only in a direction orthogonal to the surface but also a direction parallel to the surface is combined with the parabolic multilayer film monochromator. By employing this device as the in-plane diffraction measuring device (4), the analyzing system of the present invention can realize the analysis of the particle-like matter in the in-plane direction by using the in-plane X-ray scattering curve by employing the highly reliable in-plane diffraction measurement without the need for large-scale equipment. If the device disclosed in Japanese Patent Application Laid-Open No. 11-287773 is applied to the present invention, the device is not specially adjusted or changed either structurally or operationally. Therefore, reference is made to Japanese Patent Application Laid-Open No. 11-287773 for the detailed description of the structure and operation of the device.

Meanwhile, the non-uniform density sample analyzing device (3) includes a function storage means (301) which stores a scattering function (e.g., Equation 1) having fitting parameters that represent the distribution of the particles in the in-plane direction, a simulation means (302) which calculates a simulated X-ray scattering curve using the scattering function from the function storage means (301), and a fitting means (303) which performs fitting between the simulated X-ray scattering curve from the simulation means (302) and the in-plane X-ray scattering curve from the in-plane diffraction measuring device (4). Until the fitting means (303) determines that the simulated X-ray scattering curve agrees with the in-plane X-ray scattering curve, the simulation means (302) repeatedly calculates the simulated X-ray scattering curve while selecting and changing the fitting parameter by using the least square method or the like. Then, the value of the fitting parameter obtained when both of the curves agree is output, as an analysis result that represents a distribution state of the particle-like matter in the non-uniform density sample in the in-plane direction, to output means (304) and (305) such as a display, a printer, and a storage means.

In the non-uniform density sample analyzing method of the present invention, calculation steps such as simulation and fitting steps are executed by using a computer (a calculator such as a general-purpose computer or an analysis-dedicated computer). In addition, the non-uniform density sample analyzing device that the present invention also provides can be realized as, for example, software for executing functions of the above-stated means. Further, the non-uniform density sample analyzing system that the present invention further provides is preferably constituted so that data and signals can be transmitted and received between the in-plane diffraction measurement device and the non-uniform density sample analyzing device in either both or one direction.

EXAMPLE

An actual analysis result for the anisotropic non-uniform density sample will now be explained.

Figure 8:
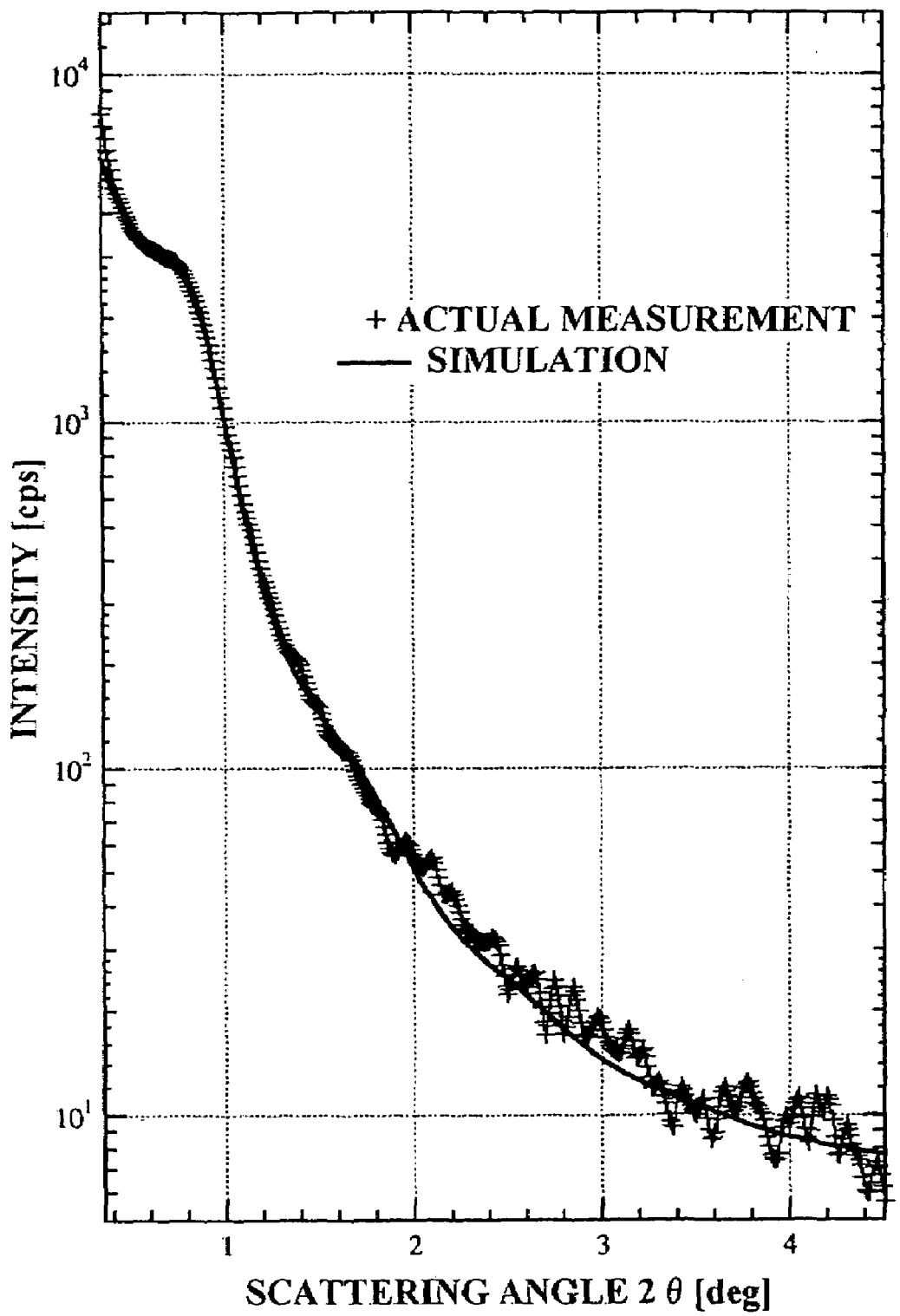
FIG. 8 illustrates a simulated X-ray scattering curve and an in-plane X-ray scattering curve as one example of the present invention.

FIG. 8 illustrates the simulated X-ray scattering curve obtained by the scattering function of Equation 1 and the in-plane X-ray scattering curve obtained by the in-plane diffraction measurement. As is obvious from FIG. 8, the excellent fitting of the both curves is realized. The fitting parameters when both of the curves agree are as follows:

Mean diameter parameter $R_o$=7.0 nm,

Distribution shape parameter M=5.0,

Shortest distance parameter D=10 nm, and

Correlation order parameter $\eta$=0.28.

Figure 9:
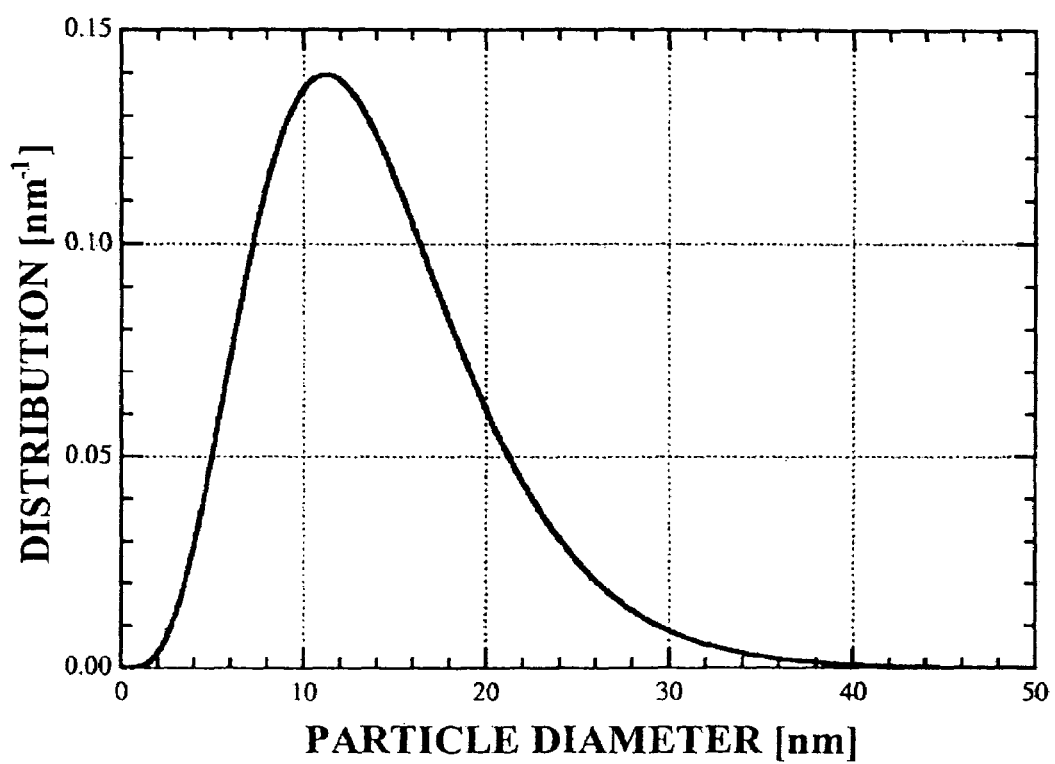
FIG. 9 illustrates a particle distribution of particles in an in-plane direction as one example.
Figure 10:
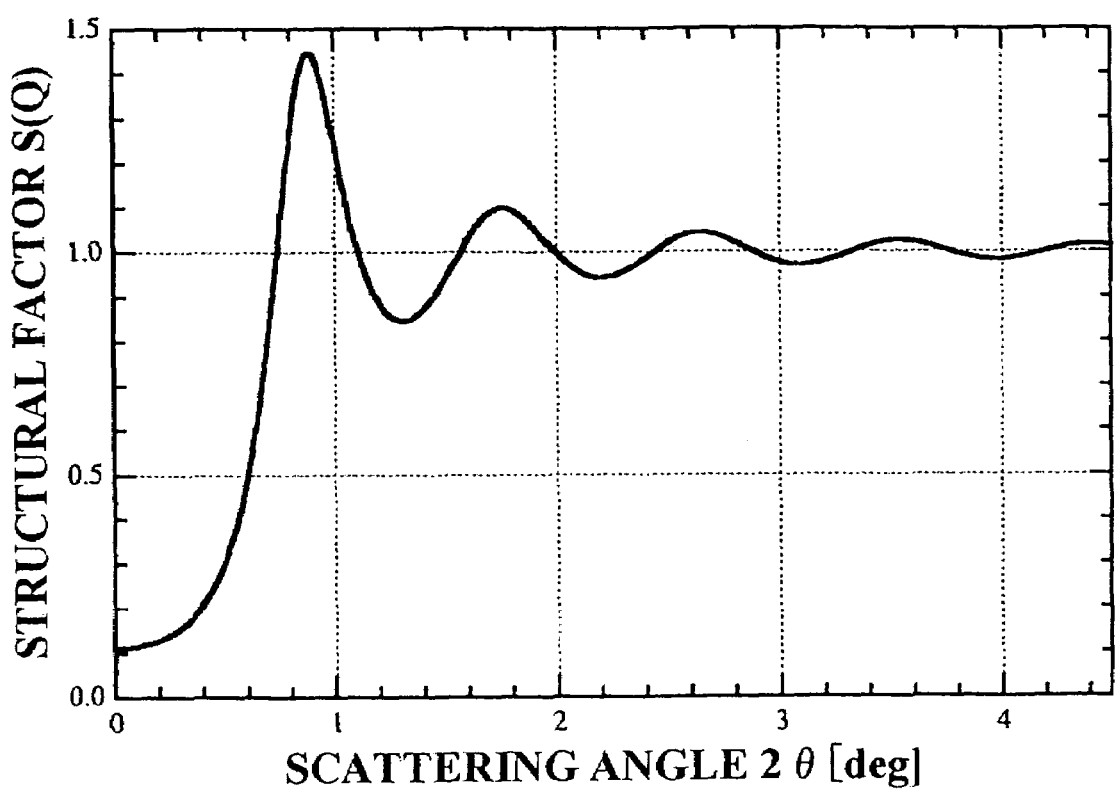
FIG. 10 illustrates a structural factor of the particle—particle correlation as one example.

These values are the mean diameter, the distribution shape, the shortest distance, and the correlation order of the particle-like matter in the anisotropic non-uniform density sample in this example. The diameter distribution of the particle-like matter in the in-plane direction is shown in FIG. 9. And, FIG. 10 illustrates the structural factor S(Q) of the particle—particle correlation.

Needless to say, this invention is not limited to the embodiment described above and various modifications can be made to details of the invention.

INDUSTRIAL APPLICABILITY

As described above in detail, according to the non-uniform density sample analyzing method, the non-uniform density sample analyzing device, and the non-uniform density sample analyzing system of the present invention, the distribution state such as the particle diameter distribution of the particle-like matter even in the anisotropic non-uniform density sample in the in-plane direction can be simply and highly accurately analyzed.

What is claimed is:

1. A non-uniform density sample analyzing method comprising:

calculating a simulated X-ray scattering curve under the same condition as a measurement condition of an actually measured X-ray scattering curve by using a scattering function which represents an X-ray scattering curve according to a fitting parameter which indicates a distribution state of particle-like matter; and carrying out fitting between the simulated X-ray scattering curve and the actually measured X-ray scattering curve while changing the fitting parameter, wherein the value of the fitting parameter when the simulated X-ray scattering curve agrees with the actually measured X-ray scattering curve serves to indicate the distribution state of the particle-like matter in a non-uniform density sample, thereby analyzing the distribution state of the particle-like matter in the non-uniform density sample, wherein the actually measured X-ray scattering curve is an in-plane X-ray scattering curve obtained by in-plane diffraction measurement, wherein the fitting is carried out between the in-plane X-ray scattering curve and the simulated X-ray scattering curve, and wherein the value of the fitting parameter when the simulated X-ray scattering curve agrees with the in-plane X-ray scattering curve serves to indicate the in-plane direction distribution state of the particle-like matter in the non-uniform density sample.

2. The non-uniform density sample analyzing method according to claim 1, wherein the fitting parameter of the scattering function indicates the in-plane direction distribution state of the particle-like matter.

3. A non-uniform density sample analyzing device, comprising:

function storage means for storing a scattering function which represents an X-ray scattering curve according to a fitting parameter which indicates a distribution state of particle-like matter;

simulation means for calculating a simulated X-ray scattering curve in the same condition as a measurement condition of an actually measured X-ray scattering curve by using the scattering function stored in said function storage means; and fitting means for carrying out fitting between the simulated X-ray scattering curve and the actually measured X-ray scattering curve while changing the fitting parameter, and wherein the value of the fitting parameter when the simulated X-ray scattering curve agrees with the actually measured X-ray scattering curve serves to indicate the distribution state of the particle-like matter in a non-uniform density sample, wherein the actually measured X-ray scattering curve is an in-plane X-ray scattering curve obtained by in-plane diffraction measurement, wherein the fitting is carried out between the in-plane X-ray scattering curve and the simulated X-ray scattering curve, wherein the value of the fitting parameter when the simulated X-ray scattering curve agrees with the in-plane X-ray scattering curve serves to indicate the in-plane direction distribution state of the particle-like matter in the non-uniform density sample, and wherein said non-uniform density sample analyzing device is operable to analyze the in-plane direction distribution state of particle-like matter having at least one of non-uniform size and shape.

4. The non-uniform density sample analyzing device according to claim 3, wherein the fitting parameter of the scattering function indicates the in-plane direction distribution state of the particle-like matter.

5. A non-uniform density sample analyzing system for analyzing a distribution state of particle-like matter in a non-uniform density sample, said system comprising:

an in-plane diffraction measuring device which performs in-plane diffraction measurement of an actually measured X-ray scattering curve for the non-uniform density sample; and a non-uniform density sample analyzing device, said non-uniform density sample analyzing device comprising:

function storage means for storing a scattering function which represents an X-ray scattering curve according to a fitting parameter which indicates a distribution state of particle-like matter;

simulation means for calculating a simulated X-ray scattering curve in the same condition as a measurement condition of an actually measured X-ray scattering curve by using the scattering function stored in said function storage means; and fitting means for carrying out fitting between the simulated X-ray scattering curve and the actually measured X-ray scattering curve while changing the fitting parameter, and wherein the value of the fitting parameter when the simulated X-ray scattering curve agrees with the actually measured X-ray scattering curve serves to indicate the distribution state of the particle-like matter in a non-uniform density sample, wherein the actually measured X-ray scattering curve is an in-plane X-ray scattering curve obtained by in-plane diffraction measurement, wherein the fitting is carried out between the in-plane X-ray scattering curve and the simulated X-ray scattering curve, wherein the value of the fitting parameter when the simulated X-ray scattering curve agrees with the in-plane X-ray scattering curve serves to indicate the in-plane direction distribution state of the particle-like matter in the non-uniform density sample, and wherein said non-uniform density sample analyzing device is operable to analyze the in-plane direction distribution state of particle-like matter having at least one of non-uniform size and shape.

6. The non-uniform density sample analyzing system according to claim 5, wherein the fitting parameter of the scattering function indicates the in-plane direction distribution state of the particle-like matter.

* * * * *